United States Patent
Sagar

(10) Patent No.: US 6,604,650 B2
(45) Date of Patent: Aug. 12, 2003

(54) BOTTLE-CAP MEDICATION REMINDER AND OVERDOSE SAFEGUARD

(75) Inventor: Richard Bryan Sagar, Santa Clara, CA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/968,343

(22) Filed: Sep. 28, 2001

(65) Prior Publication Data

US 2003/0063522 A1 Apr. 3, 2003

(51) Int. Cl.[7] ............................................. G07F 11/00
(52) U.S. Cl. ........................................... 221/3; 700/244
(58) Field of Search ................................. 221/2, 3, 7, 9, 221/15, 97, 191, 82, 129; 700/231, 244; 340/870.09, 309.15

(56) References Cited

U.S. PATENT DOCUMENTS

| | | | | |
|---|---|---|---|---|
| 4,626,105 A | * | 12/1986 | Miller | 368/10 |
| 5,392,952 A | * | 2/1995 | Bowden | 221/15 |
| 6,138,865 A | * | 10/2000 | Gilmore | 221/2 |
| 2002/0097156 A1 | * | 7/2002 | Broas | 340/573.1 |

* cited by examiner

Primary Examiner—Kenneth W. Noland
(74) Attorney, Agent, or Firm—Peter Zawilski

(57) ABSTRACT

A medicine-dispensing system has a medication reminder to assist the patient in following a drug regimen. In an example embodiment, a medication reminder comprises a timer programmable to a predetermined interval. A user-alert is responsive to the timer, reminding the user to take a dose of medicine at the predetermined interval. A sensor detects whether a dose of medicine has been taken and a dose-indication informs the user of the time since a last medication. The dose indication further informs the user as to whether to take a next medication dose. Time of the last dose is determined by the timer receiving a signal from the sensor. A communications interface enables programming of a parameter associated with administering a medication.

7 Claims, 4 Drawing Sheets

BOTTLE-CAP MEDICATION REMINDER AND OVERDOSE SAFEGUARD

FIELD OF INVENTION

The present invention is generally directed toward to the dispensing of product for a user. In particular, the present invention relates to the dispensing of medication for a patient using reminder and overdose safeguard incorporated into a medicine container.

BACKGROUND OF INVENTION

The advances in medicine are enhancing the quality of patients' lives. Ailments, for which only a few years ago, there were no effective treatments are now taken care of by one or more drugs. In many cases, the patient only has to remember to take a pill over prescribed intervals, for example three times daily. However, a number of ailments required treatment with one or more combinations of (oral) medication.

With most medication (e.g., pills, syrups), doses have to be taken at specific intervals (Every four-six hours) or times of day (Before meals). A person may have difficulty remembering to take medication, sometimes people have difficulty remembering that they have already taken a dose. The result may be either that the amount of medicine taken is too low to affect the course of the ailment or that the amount is too high and causes overdose reactions. In a multiple drug regimen, such a scenario is even more convoluted and may pose grave consequences to the patient.

There exists a need to prevent the improper dosing of medication and to help the patient follow his/her drug regimen.

SUMMARY OF INVENTION

The compliance with a drug regimen to treat a particular ailment is significant in achieving a successful outcome. Maintaining an efficacious level of the drug rests with taking a proper dose at the appropriate intervals. The present invention is exemplified in a number of implementations, a number of which are summarized below.

In one embodiment according to the present invention, a container comprises an interface part for enabling a user to be reminded of taking a dose of a substance in the container. The interface part comprises a timer and a user-alert generator coupled to the timer for generating an alert upon a predetermined time interval. An additional feature of the embodiment is that it further comprises a sensor to detect whether a closure has been removed from the container. A dose-indication informs the user of the time since a last substance dose. The dose indication further informs the user as to whether to take a next substance dose, the time of the last dose determined by the timer receiving a signal from the sensor. Yet, another additional feature the embodiment is that the container further comprises a communications interface enabling programming of a parameter associated with the alert to administer the substance.

In another embodiment according to the present invention, there is a method of reminding to administer a dose of medication. The method comprises sending a reminder via a portable electronic device; and enabling the device to receive the reminder.

In yet another embodiment of the present invention, a service is on a communication network for sending a control message to an electronic device for causing the device to generate a reminder. The device confirms to the service receipt of the control message. Then the service sets a time for a next control message upon receipt of the confirmation.

The above summaries of the present invention are not intended to represent each disclosed embodiment, or every aspect, of the present invention. Other aspects and example embodiments are provided in the figures and the detailed description that follows.

BRIEF DESCRIPTION OF THE DRAWINGS

The invention may be more completely understood in consideration of the following detailed description of various embodiments of the invention, giving by way of example, in connection with the accompanying drawing, in which.

Figure 1:
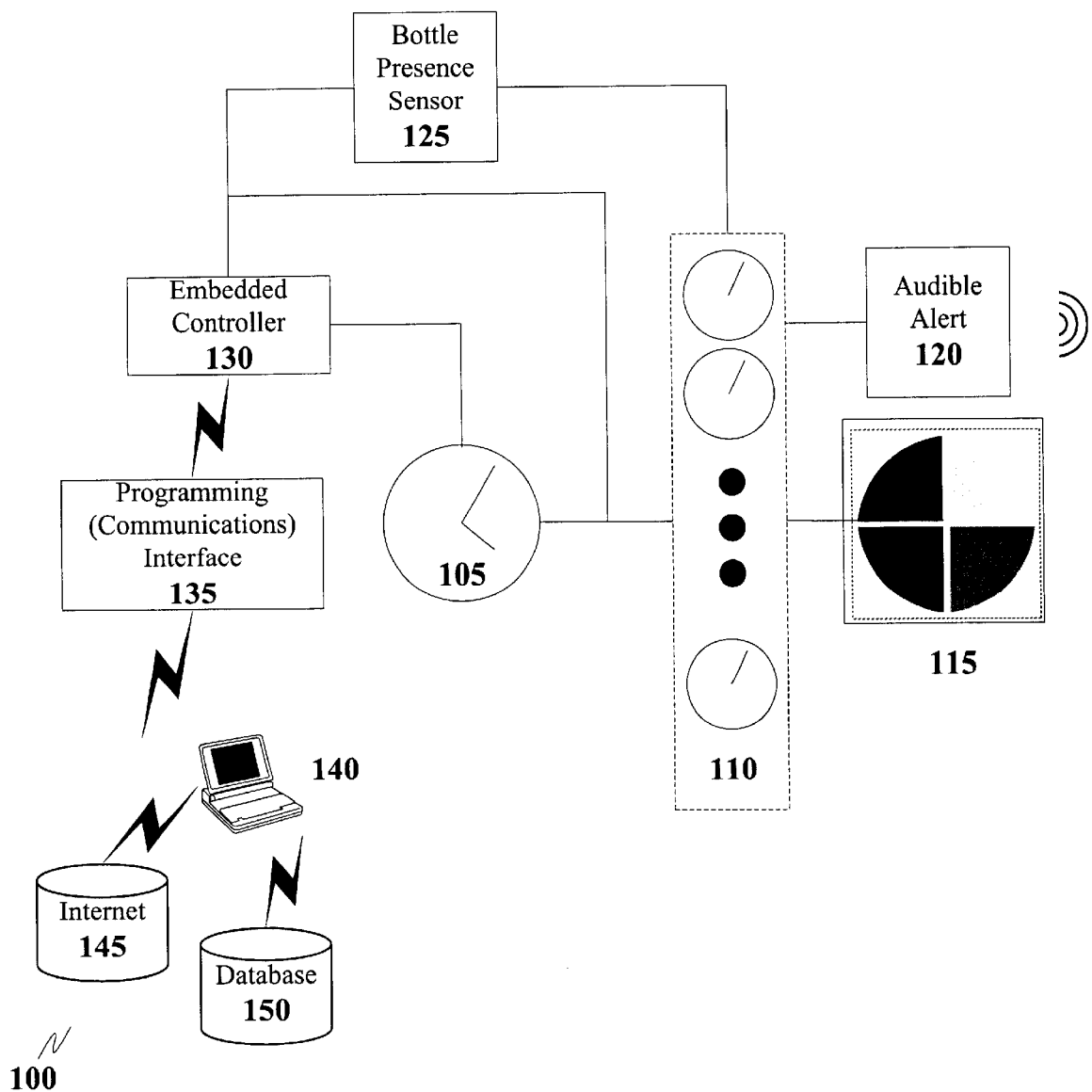
FIG. 1 is a block diagram of the operation of the medicine bottle closure according to an embodiment of the present invention.

While the invention is susceptible to various modifications and alternative forms, specific embodiments thereof have been shown by way of example in the drawing and will herein be described in detail.

DETAILED DESCRIPTION

The present invention has been found to be useful in the dispensing of pharmaceuticals to patients or other users. A user is not necessarily a patient (i.e, someone suffering from an ailment). One may prescribe a drug as a prophylaxis. For example, when one is travelling to a part of the world in which malaria is endemic, it is prudent to take anti-malarial compounds to prevent the onset of disease.

In many drug regimens, it is necessary to maintain a steady level of a particular drug to assure efficacy. For example, if pills are prescribed and one pill must be taken at an interval of every four hours, the benefits of the medication is assured if the user takes it as close to the interval as practicable. A reminder apparatus integrated with the medicine's container provides a visual status of pills taken or not taken during the day.

In an example embodiment according to the present invention, a pill bottle cap has built in the following:

Real-time clock
One or more timers
Audible alert
Display (for example, a 2 or 3 color LCD)
Sensor to detect presence of bottle
Button or buttons
Electrical communications interface (for programming)
Battery Refer to FIG. 1. The block diagram 100 provides an overview of the components of an embodiment of the present invention. A real-time clock 105 provides a time base reference for the interval timers 110. One timer represents an interval at which a dose must be taken. For example, a medication requiring four daily doses would have a timer corresponding to each dose, therefore four timers. However, the invention is not so limited. An alert 120 to inform the user of a dose may be audible tome or be a visual display, or be a tactile signal. A graphical user interface (GUI) 115 provides the user a graphical display of the status of each dose of medication. The GUI 115 typically is a liquid crystal display (LCD). To detect cap removal there is a sensor 125. One or more buttons 140 enable the user to check the status of the dosages taken or available, or may be used to program the device via a programming interface 135. The programming interface 135 enables the pharmacist to download the dosage intervals and other pertinent information from a computing device such as computer 145. The programming interface 135 may be a plugged-in connection, a wireless transmitter with the receiver integral to the present invention, or an infrared interface. Such information may include, but not be limited to, the dosage, the number of pills, the interval, etc. Information relevant to the prescription is retrieved from a local database 150 or a database residing on the Internet 145. An embedded controller 130 within the bottle cap coordinates the activities of the aforementioned components. A battery (not illustrated) provides power.

To prevent a user missing a dose, multiple timers 110 are set, one for each time that medication must be taken. Timers 110 activate the audible alert 120 when the dose is due. The audible alert 120 is only cancelled by removal of cap from bottle, however, a snooze feature may be implemented using a button, to allow the patient to temporarily silence alert (for 15 minutes), for convenience. Removal of cap is signaled by bottle presence sensor 125. Such a sensor may be mechanical, for example, a switch that is actuated upon opening and closing of the bottle. In another embodiment, in that many medications are packaged in tinted containers, usually brown, to protect them from light degradation, an optical sensor in the cap may detect the change in the intensity of the light it receives. The cap on the bottle may receive little light and while the cap off the bottle may receive more light. The optical sensor then provides an "cap on" or "cap off" indication.

Figure 2A:
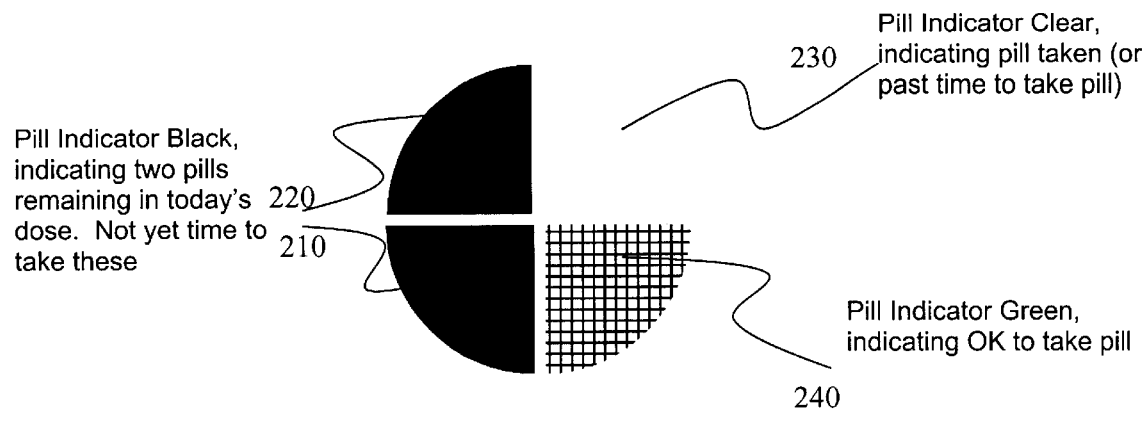
FIG. 2A depicts a medicine bottle closure of FIG. 1 with a graphical display of the daily dosage of a medication, pill indicator green, okay to take pill but early.
Figure 2B:
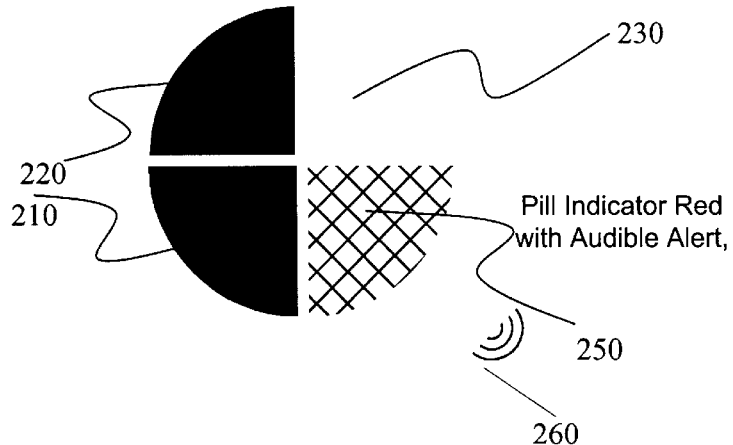
FIG. 2B depicts the graphical display of FIG. 2A but pill indicator red with audible alert, take pill immediately.

Refer to FIGS. 2A and 2B. To prevent overdose, the liquid crystal display (LCD) of the pill indicator 200 is used to show a graphical representation of the number of pills that should be taken in a day, along with an indication of the number already taken. Color may be used to show whether it is safe to take the next dose now, i.e., early. For instance, if the usage states "Doses to be taken every 4–6 hours," then the color of the next indicator might change according to the following table.

TABLE 1

Indication of Safety to Take Next Dose

| Time Since Last Dose | Indicator Color Next Pill | Meaning |
|---|---|---|
| 0–4 hours | Black (210, 220) | Do not take (too early) |
| 4–5.5 hours | Green (240) | Safe to take, but early |
| 5.5–6 hours | Red (250) | Good time to take |
| 6 hours | Red (260) + audible alert | Take immediately |
| 6+ hours | Clear (230) | Do not take (missed dose) |

The cap would use the time it was last removed (as detected by the sensor) as the datum for the Time since last dose.

If the pill indicator 200 displays black (210, 220) it shows that two pills remain in today's dose. It is not the time to take these. If pill indicator 200 displays green 240, it is safe to take a pill, but it is early (FIG. 2A). A red display 250 indicates it is a good time to take the pill. The red display 250, with an audible alert 260 means the patient should take the pill immediately (FIG. 2B). A clear display 230 means that the dose has been taken or missed and must not be taken now. To compensate for color-blindness in some individuals, the pill indicator 200 display, sections (210, 220, 230, 240, or 250) may employ hatch patterns or large numerals that change in appearance.

In another embodiment according to the present invention, information relevant to the patient's prescription may be downloaded into the bottle-cap medication reminder via a portable digital assistant, a personal computer, or wireless phone equipped with an infrared port. These devices in turn are connected to a network so that they have access to the prescription information.

Figure 3:
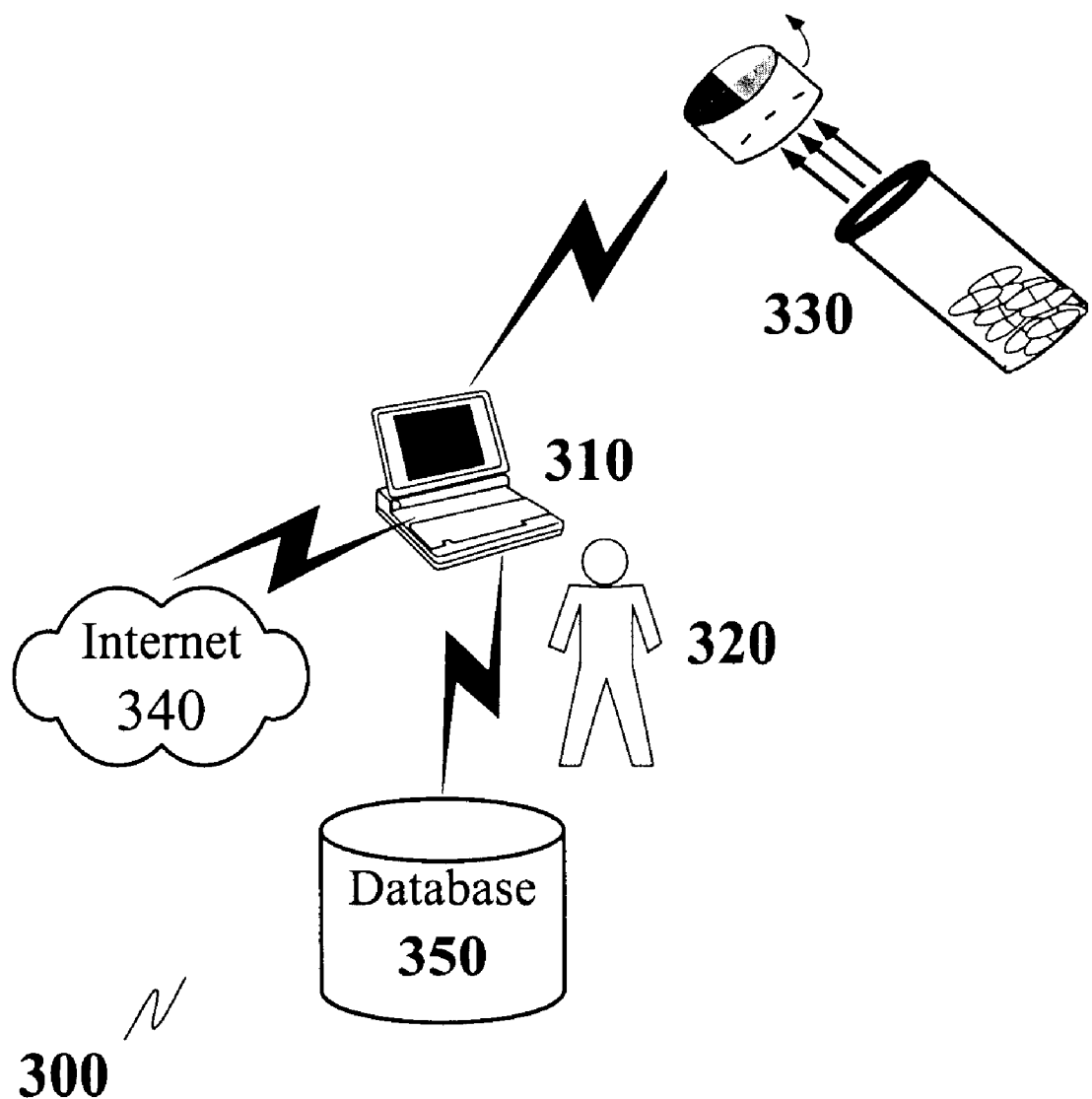
FIG. 3 depicts the Pharmacist programming of the medicine bottle according to an embodiment of the present invention.

FIG. 3 illustrates a process 300 of programming the bottle cap 330. Pharmacist 320 at his laptop computer 310 downloads the prescription information into the bottle cap 330. The bottle cap 330 is in communication with the laptop 310. The laptop computer 310 is in communication with a prescription database 350 either local or on a remote server on the Internet 340. The bottle cap 330 contains the prescription information programmed therein. Such programmed information also appears as a printed conventional label that is applied to the bottle. In another embodiment, the functionality of the bottle cap 330 may also be embedded in a semiconductor chip that is integral to the prescription label.

The prescription information shown on the display of the medication reminder may be mimicked on the PDA, PC, or wireless phone. The user receives the reminder through these devices, as these devices are personal and trusted. The hospital or pharmacy may implement the reminder as a service to enhance follow-up care and ensure compliance with the drug regimen. Additionally, the personal electronic devices may assure that the bottle-cap reminder is up-to-date and synchronized-not unlike the data stored in a PDA being synchronized with the backup data stored in the user's PC.

Figure 4:
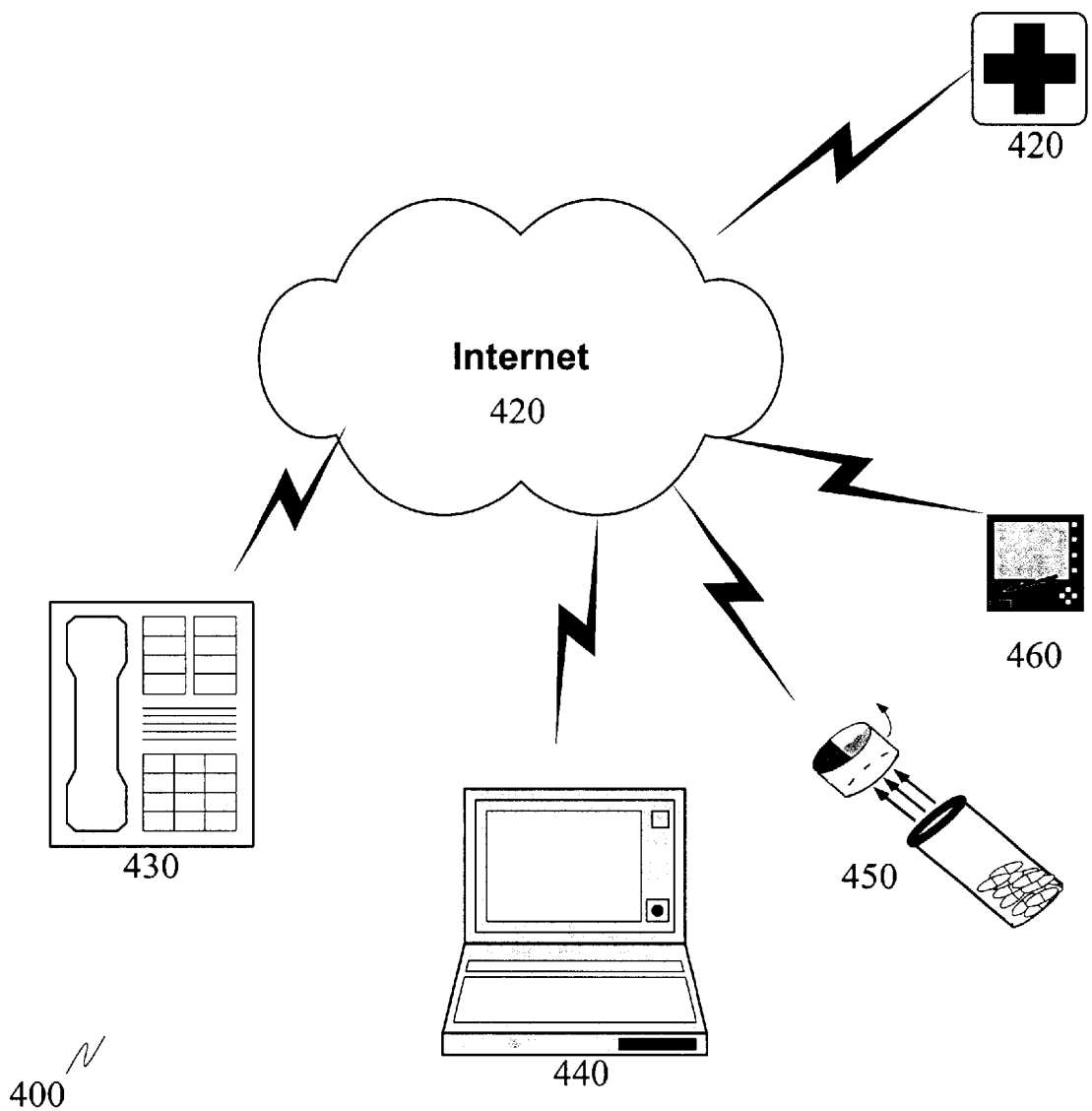
FIG. 4 depicts the reminding of the patient to take medication via an Internet-based service.

Refer to FIG. 4. The user in his connection to the Internet realm 400 may have several devices in communication with the Internet 420. For example, the pharmacy or doctor 420 may send a reminder to the user as a phone call 430. The patient may receive an E-mail at his computer workstation 440 or his PDA 460. The bottle cap 450 itself may receive the reminder directly. Again, this functionality may exist as a "smart label" on the medicine's packaging as well.

While the present invention has been described with reference to several particular example embodiments, those skilled in the art will recognize that many changes may be made thereto without departing from the spirit and scope of the present invention, which is set forth in the following claims.

What is claimed:

1. A container comprising an interface part for enabling a user to be reminded of taking a dose of a substance in the container, the interface part comprising:
   a timer; and
   a user-alert generator coupled to the timer for generating an alert upon a predetermined time interval, the user-alert generator further comprises,
      a sensor to detect whether a closure has been removed from the container; and
      a dose-indication informing the user of the time since a last substance dose was taken, the dose-indication farther informing the user as to whether to take a next substance dose, the time of the last dose being determined by the timer receiving a signal from the sensor.

2. The container of claim 1, further comprising:

a communications interface enabling programming of a parameter associated with the alert to administer the substance.

3. The container of claim 2, wherein the communications interface enables the programming via at least one of the following: a PDA, a laptop computer, a desktop computer, a wireless telephone.

4. A medication reminder system, comprising:

a timer programmable to a predetermined interval;

a user-reminder responsive to the timer, for reminding the user to take a dose of medicine upon the predetermined interval having elapsed;

a sensor to detect whether a dose of medicine has been taken, the sensor comprising a switch for detecting when a closure is removed from the medicine container; and a dose-indicator informing the user as to whether to take a next medication dose, the time of the last dose being determined by the timer receiving a signal from the sensor; and a communications interface enabling programming of a parameter associated with administering the medication.

5. The medication reminder system of claim 4, wherein the communications interface enables programming the timer via at least one of the following: a PDA, a laptop computer, a desktop computer, a wireless telephone.

6. The medication reminder system of claim 4 wherein, the sensor further comprises at least one of the following switch types: optical, mechanical, magnetic.

7. The medication reminder system of claim 6 wherein the medication reminder system with at least one of the following: the closure, the medicine container.

* * * * *